US00PP28137P2

(12) United States Plant Patent
Zaiger et al.

(10) Patent No.: US PP28,137 P2
(45) Date of Patent: Jun. 27, 2017

(54) INTERSPECIFIC TREE NAMED 'HERMOSA'

(50) Latin Name: ***Interspecific Prunus* species**
Varietal Denomination: Hermosa

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 14/999,266

(22) Filed: Apr. 18, 2016

(51) Int. Cl.
*A01H 5/08* (2006.01)

(52) U.S. Cl.
USPC ..... Plt./180

(58) Field of Classification Search
USPC ..... Plt./180
CPC ..... A01H 5/0837
See application file for complete search history.

*Primary Examiner* — Kent L Bell

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree having a vigorous, semi-spreading growth habit.
2. Tree being a regular and productive bearer of medium to large size fruit.
3. Fruit with an attractive orange skin color.
4. Fruit with very good flavor and eating quality.

1 Drawing Sheet

Botanical designation: Interspecific *Prunus* species.
Variety denomination: 'Hermosa'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

Prior Varieties

Among the existing varieties of interspecific trees, which are known to us, and mentioned herein, 'Escort' Interspecific (U.S. Plant Pat. No. 18,537) and our proprietary non-patented interspecific seedling selections '57MC594', '32ZH874', '12ZB628', '305LN566', '177LM433' and '13M205'.

STATEMENT REGARDING FEDERALLY SPONSORED RESEARCH AND DEVELOPMENT

Not applicable.

ORIGIN OF THE VARIETY

The new variety of interspecific tree, a combination of crosses between *Prunus armeniaca* and *Prunus salicina* was originated by us in our experimental orchard located near Modesto, Calif. from crosses between the proprietary non-patented interspecific varieties with the field identification numbers '57MC594' and '32ZH874'. The seed parent (57MC594) originated as a first generation seedling selection from the cross of the non-patented interspecific seedlings '12ZB628' and '305LN566'. The pollen parent (32ZH874) originated as a first generation seedling selection from the cross of our proprietary non-patented interspecific seedlings '177LM433' and '13M205'. A large number of these first generation seedlings were budded onto older established trees of 'Nemaguard' Rootstock (non-patented) to enhance earlier fruit production. Under close and careful observation the present seedling exhibited desirable fruit and tree characteristics and was selected in 2010 for additional asexual propagation and commercialization.

ASEXUAL REPRODUCTION OF THE VARIETY

In 2010 asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct variety of interspecific tree, which consists of multiple crosses between Apricots and Plums, is of large size, vigorous, semi-spreading growth and a regular and productive bearer of medium to large size, orange flesh, freestone fruit. The fruit is further characterized by having an attractive orange skin color, very good flavor and eating quality. In comparison to its proprietary non-patented interspecific seed parent '57MC594' the fruit of the new variety is larger in size and is approximately 51 days earlier in maturity. In comparison to its proprietary non-patented pollen parent '32ZH874' the fruit of the new variety is larger in size and approximately 13 days earlier in maturity. In comparison to the commercial variety 'Escort' Interspecific (U.S. Plant Pat. No. 18,537) the fruit of the new variety is approximately 20 days later in maturity.

DESCRIPTION OF THE PHOTOGRAPH

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 5 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 5 year old specimens grown near Modesto, Calif., with color in accordance with Munsell Book of Color published in 1958.

Tree:

*Size*.—Large, usually pruned to 3 to 3.5 meters in height and width for economical harvesting of fruit. Varies with different cultural practices.

*Vigor*.—Vigorous, tree growth of approximately 1.5 to 2 meters the first growing season. Varies with cultural practices, soil type, fertility of soil and climatic conditions.

*Form*.—Semi-spreading, usually pruned to vase shape.

*Branching habit*.—Semi-spreading, crotch angle approximately 35°, increases with heavy crop load.

*Productivity*.—Productive, thinning and spacing of fruit necessary for desired market size. Number of fruit set varies with climatic conditions during blooming period.

*Bearer*.—Regular, has had adequate fruit set 3 consecutive years. No alternate bearing observed.

*Fertility*.—Self fertile, sets fruit under bag.

*Density*.—Medium dense, usually pruned to vase shape to increase air movement and sunlight to center of tree to enhance fruit color and health of fruit spurs.

*Hardiness*.—Hardy in all stone fruit growing areas of California. Tree grown in USDA Hardiness Zone 9. Winter chilling requirement approximately 800 hours at or below 45° F.

Trunk:

*Size*.—Medium to large. Average circumference 55.9 cm at 25.4 cm above ground on a 5 year old tree.

*Stocky*.—Medium stocky.

*Texture*.—Medium shaggy, roughness increases with age.

*Color*.—Varies from 5GY 5/2 to 2.5Y 3/2.

Branches:

*Size*.—Large. Average circumference 14.7 cm at 1.2 meters above ground. Crotch angle approximately 35°, increases with heavy crop load.

*Surface texture*.—New growth relatively smooth. Mature growth medium rough, roughness increases with age.

*Lenticels*.—Average number 27 in a 25.8 square cm area. Average length 3.6 mm. Average width 1.4 mm. Color varies from 7.5YR 6/12 to 5YR 6/12.

*Color*.—New growth varies from 7.5GY 5/6 to 2.5YR 3/4 where exposed to the sun. Mature growth varies from 2.5YR 3/6 to 5YR 3/6, varies with age of growth.

Leaves:

*Size*.—Medium. Average length 80.1 mm. Average width 59.4 mm.

*Form*.—Ovate.

*Apex*.—Acuminate.

*Base*.—Cuneate.

*Margin*.—Doubly serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Large. Average length 33.3 mm. Average width 1.2 mm. Longitudinally grooved. Surface — glabrous. Color varies from 2.5GY 7/4 to 2.5GY 5/4.

*Glands*.—Type — reniform. Size — small. Average length 1.0 mm. Average diameter 0.7 mm. Average number 2, varies from 1 to 3. Located primarily on the upper portion of the petiole and base of leaf blade. Color varies from 10R 3/6 to 2.5YR 3/6.

*Stipules*.—None present at time of measurements.

*Color*.—Upper surface varies from 7.5GY 3/4 to 5GY 3/6. Lower surface varies from 5GY 4/4 to 7.5GY 4/4. Midvein varies from 2.5GY 6/6 to 10Y 7/4.

Flower buds:

*Size*.—Large. Average length 13.8 mm. Average diameter 9.4 mm.

*Hardiness*.—Hardy with respect to California winters.

*Density*.—Medium dense.

*Form*.—Conical, becoming elongated just before opening.

*Pedicel*.—Average length 2.4 mm. Average width 1.1 mm. Surface- glabrous. Color varies from 2.5GY 7/8 to 5GY 7/8.

*Color*.—Varies from 5RP 9/2 to 5RP 8/6.

*Number of buds per spur*.—Varies from 4 to 11, average number 7.

Flowers:

*Blooming period*.—Date of First Bloom Feb. 14, 2015. Date of Petal Fall Feb. 24, 2015, varies slightly with climatic conditions.

*Size*.—Medium to large. Average height 17.4 mm. Average diameter 27.2 mm.

*Petals*.—Normally 5, alternately arranged to sepals. Size — medium. Average length 15.3 mm. Average width 15.2 mm. Shape — orbicular. Arrangement — overlapping. Petal apex — rounded. Petal base — truncate. Margin — sinuate. Color varies from N 9.5/(white) to 5RP 9/2. Both upper and lower surfaces glabrous.

*Sepals*.—Normally 5, alternately arranged to petals. Size — medium. Average length 6.8 mm. Average width 6.8 mm. Shape — ovate, apex rounded to triangular. Margin — entire. Both upper and lower surfaces glabrous. Color — upper surface varies from 10RP 7/4 to 10RP 3/10. Lower surface varies from 10RP 4/14 to 10RP 3/10.

*Stamens*.—Average number per flower 31. Average filament length 11.8 mm. On average the stamens are even with the height of the petals. Filament color N 9.5/(white). Anther color varies from 5Y 8.5/10 to 5Y 8/8.

*Pollen*.—Self fertile, sets fruit under bag. Color varies from 2.5Y 7/12 to 5Y 7/12.

*Pistil*.—Number — normally one. Average length 14.8 mm. On average, the position of the stigma is 1.2 mm below anthers. Surface — pubescent. Color varies from 5Y 8.5/4 to 7.5Y 8/4.

*Fragrance*.—Heavy aroma.

*Color*.—Varies from 5RP 9/2 to N 9.5/(white).

*Pedicel*.—Average length 2.7 mm. Average width 1.1 mm. Color varies from 5GY 8/6 to 5GY 6/10.

*Number flowers per flower bud*.—Average 2, varies from 1 to 3.

Fruit:

*Maturity when described*.—Firm ripe and ready for consumption.

*Date of first picking*.—Jun. 27, 2015.

*Date of last picking*.—Jul. 7, 2015, varies slightly with climatic conditions.

*Size*.—Medium to large. Average diameter axially 63.3 mm. Average transversely in suture plane 61.7 mm. Average across suture plane 57.1 mm. Average weight 130.6 grams, varies slightly with fertility of the soil, amount of thinning and climatic conditions.

*Form*.—Globose.

*Suture*.—Slightly lipped, extends from base toward apex.

*Ventral surface*.—Slightly lipped.

*Apex*.—Slightly retuse.

*Base*.—Flat to slightly retuse.

*Stem cavity*.—Rounded to slightly elongated in suture plane. Average depth 6.5 mm. Average diameter 3.7 mm.

Stem:

*Size*.—Small. Average length 9.5 mm. Average diameter 3.2 mm.

*Color*.—Varies from 5GY 6/6 to 5GY 5/6.

Flesh:

*Ripens*.—Evenly.

*Texture*.—Firm, meaty.

*Fibers*.—Few, small, tender.

*Firmness*.—Firm, comparable to other commercial apricot varieties.

*Aroma*.—Slight.

*Amydgalin*.—Undetected.

*Eating quality*.—Very good.

*Flavor*.—Very good, with a good balance between acid and sugar.

*Juice*.—Moderate amount, enhances flavor.

*Acidity*.—Not available.

*Brix*.—Average Brix 16.0°, varies slightly with amount of fruit per tree and climatic conditions.

*Color*.—Varies from 7.5YR 6/12 to 6.25YR 7/12.

*Pit cavity*.—Average length 35.0 mm. Average width 26.3 mm. Average depth 8.7 mm. Color 6.25YR 6/12.

Skin:

*Thickness*.—Medium.

*Surface*.—Smooth to slightly waffled.

*Pubescence*.—Moderate amount, short in length.

*Tendency to crack*.—None.

*Color*.—Color varies from 2.5YR 6/12 to 5YR 6/10.

*Tenacity*.—Tenacious to flesh.

*Astringency*.—Slight to none.

Stone:

*Type*.—Freestone, weak adherence to flesh.

*Size*.—Large. Average length 33.0 mm. Average width 24.3 mm. Average thickness 15.3 mm.

*Form*.—Ovoid.

*Base*.—Flat.

*Apex*.—Rounded.

*Surface*.—Lightly pitted throughout. One shallow groove on each side of suture extending from base toward apex.

*Sides*.—Unequal, one side extending further outward from suture plane.

*Ridges*.—Very small and short, extending from base towards apex.

*Tendency to split*.—None.

*Color*.—Varies from 7.5YR 3/2 to 7.5YR 3/4 when dry.

Kernel:

*Size*.—Large. Average length 21.3 mm. Average width 14.3 mm. Average depth 9.3 mm.

*Form*.—Ovoid.

*Viability*.—Viable, complete embryo development.

*Skin color*.—Varies from 5Y 9/4 to 7.5Y 9/4.

Use: Dessert.

*Market*.—Local and long distance.

Keeping quality: Good, held firm in cold storage for 3 weeks at 38° to 42° F. without shriveling, internal breakdown of flesh or appreciable loss of eating quality.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program. No atypical resistances/susceptibilities have been noted under normal cultural practices. The present new variety of interspecific tree, its flowers foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

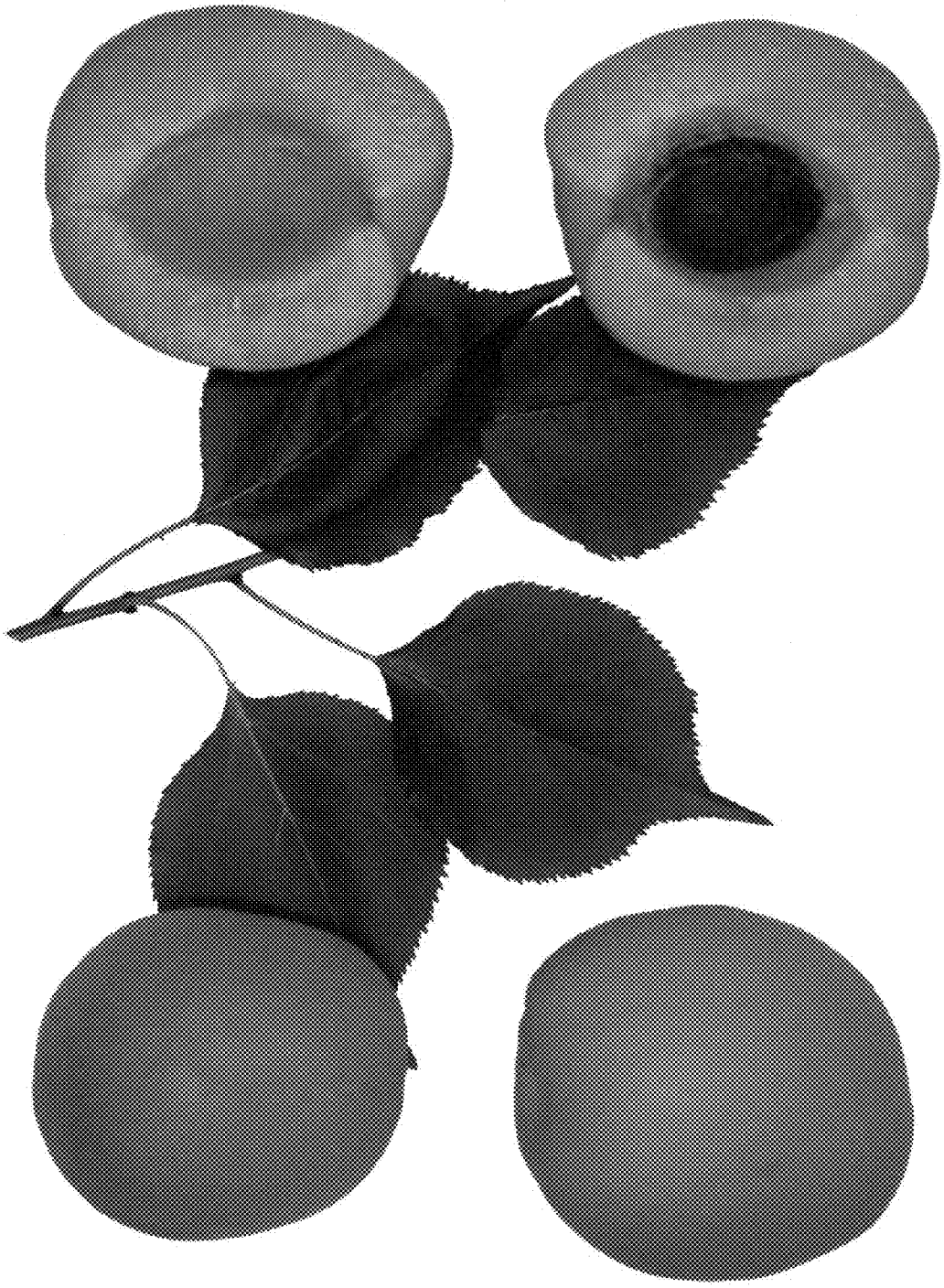

* * * * *